United States Patent
Ashparie et al.

(10) Patent No.: US 10,014,080 B2
(45) Date of Patent: *Jul. 3, 2018

(54) EVIDENCE BASED MEDICAL RECORD

(71) Applicant: International Business Machines Corporation, Armonk, NY (US)

(72) Inventors: Yousuf M. Ashparie, Centreville, VA (US); Aaron K. Baughman, Silver Spring, MD (US); Brenda L. Dietrich, Somers, NY (US); Arnold Greenland, Silver Spring, MD (US); Peter K. Malkin, Ardsley, NY (US); Palani Sakthi, Palantine, IL (US)

(73) Assignee: International Business Machines Corporation, Armonk, NY (US)

( * ) Notice: Subject to any disclaimer, the term of this patent is extended or adjusted under 35 U.S.C. 154(b) by 250 days.

This patent is subject to a terminal disclaimer.

(21) Appl. No.: 14/946,471

(22) Filed: Nov. 19, 2015

(65) Prior Publication Data

US 2016/0078188 A1 Mar. 17, 2016

Related U.S. Application Data

(63) Continuation of application No. 14/085,238, filed on Nov. 20, 2013, now Pat. No. 9,292,658.

(51) Int. Cl.
*G16H 50/20* (2018.01)
*G06F 19/00* (2018.01)
(Continued)

(52) U.S. Cl.
CPC ........... *G16H 50/20* (2018.01); *G06F 19/322* (2013.01); *G06F 19/345* (2013.01);
(Continued)

(58) Field of Classification Search
None
See application file for complete search history.

(56) References Cited

U.S. PATENT DOCUMENTS

| | | |
|---|---|---|
| 7,801,740 B1 | 9/2010 | Lesser |
| 2002/0010679 A1 | 1/2002 | Felsher |

(Continued)

OTHER PUBLICATIONS

Notice of Allowance and Fee(s) Due for U.S. Appl. No. 14/085,238, dated Dec. 9, 2016, 5 pages.
(Continued)

*Primary Examiner* — Alan Chen
(74) *Attorney, Agent, or Firm* — Daniel Simek; Hoffman Warnick LLC

(57) ABSTRACT

Various embodiments provide systems, computer program products and computer implemented methods. In some embodiments, a system includes a method of providing a confidence-estimation-based inference, the method includes receiving a query concerning a patient from a user, accessing an electronic health record (EHR) for the patient, the EHR including a first component regarding the patient, querying the user, using a conversational interface, for a second component regarding the patient, receiving the second component regarding the patient in response to the query, calculating a first probability density function using the first component, and a second probability density function using the second component, combining the first and second probability density functions using a Gaussian mixture model, calculating at least one conditional probability table using the Gaussian mixture model and providing the confidence-estimation-based inference based on the at least one conditional probability table.

20 Claims, 7 Drawing Sheets

(51) Int. Cl.
*G16H 50/50* (2018.01)
*G16H 10/60* (2018.01)
*G06N 7/00* (2006.01)

(52) U.S. Cl.
CPC ......... *G06F 19/3437* (2013.01); *G06N 7/005* (2013.01); *G16H 10/60* (2018.01); *G16H 50/50* (2018.01)

(56) References Cited

U.S. PATENT DOCUMENTS

| | | |
|---|---|---|
| 2004/0220895 A1 | 11/2004 | Carus et al. |
| 2008/0201429 A1 | 8/2008 | Barbell et al. |
| 2009/0089100 A1 | 4/2009 | Nenov et al. |
| 2010/0241595 A1 | 9/2010 | Felsher |
| 2011/0004110 A1 | 1/2011 | Shusterman |
| 2012/0101847 A1 | 4/2012 | Johnson et al. |
| 2012/0165618 A1 | 6/2012 | Algoo et al. |
| 2013/0124523 A1 | 5/2013 | Rogers et al. |

OTHER PUBLICATIONS

Luz et al., "Locating Case Discussion Segments in Recorded Medical Team Meetings", Copyright 2009, ACM.

Barnett, "History of the Development of Medical Information Systems at the Laboratory of Computer Science at Massachusetts General Hospital", Copyright 1987, ACM.

Barschdorff, Automatic Assessment of an "Apnoea-Severity-Factor" combined with Heart Rate Analysis during Polysomnographic Examination in Infants, Computers in Cardiology, 1994.

Takemura et al., "An Extraction of Medical knowledge on Text Mining for Ubiquitous Medicine", Copyright 2004, IEEE.

Newman et al., "Pausing in doctor-patient conversation during computer use: The design significance of their durations and accompanying topic changes", International Journal of Human-Computer Studies, 68 (2010) 398-490.

Dong et al., "Automatic Extraction of Femur Contours from Calibration X-Ray Images using Statistical Information", Journal of Multimedia, vol. 2, No. 5, Sep. 2007.

Karavatselou et al., "OTE-TS—A New Value-Added Telematics Service for Telemedicine Applications", IEEE Transactions on Information Technology in BioMedicine, vol. 5, No. 3, Sep. 2001.

Altowaijri et al., "A Quantitative Model of Grid Systems Performance in Healthcare Organisations", 2010 International Conference on Intelligent Systems, Modelling, and Simulation.

Ebert et al., "Spike Analysis Framework: An Approach to Flexible Neuronal Cell Analysis", 2011 IEEE.

Piras et al., Prescriptions, X-rays, and Grocery Lists: Designing a Personal Health Record to Support (The Invisible Work of) Health Information Management in the Household, Computer Supported Cooperative Work: The Journal of Collaborative Computing, vol. 19, No. 6, Dec. 2010.

Takemura et al., "A Study of the Medical Record Interface to Natural Language Processing", Journal of Medical Systems, vol. 26, No. 2, Apr. 2002.

Unknown, "Clinical Documentation: Driving Performance in the New World of Healthcare", Copyright 2013, Nuance Communications Inc.

Non Final Office Action for U.S. Appl. No. 14/085,238, dated Oct. 23, 2015, 11 pages.

EVIDENCE BASED MEDICAL RECORD

FIELD

The subject matter disclosed herein relates generally to medical records. More particularly, the subject matter disclosed relates to providing a confidence-based inference from evidence-based medical records and natural language input.

BACKGROUND

In general, Electronic Health Record (EHR) can be used to store patient data for future recovery to assist in treatment plans. An EHR typically contains a variety of medical information related to a patient. The information may include family history, genomic decoding, phenotype expressions, epigenetic reactions, and vitality information in the form of text and multimedia information. A physician may use the information in an EHR to determine a diagnosis, a prognosis, or for general patient health monitoring. Currently, EHRs provide standardized, accessible, and instantaneous patient data that may be used by medical practitioners in health care settings.

Some natural-language-using, interactive computing systems, referred to as Natural Language Processing (NLP) systems may be used to communicate with humans. Currently, NLP systems may be used to provide answers to natural-language questions. However, a link between and EHRs and NLP systems is not yet defined.

BRIEF DESCRIPTION

Various aspects of the invention provide for systems, computer program products and computer implemented methods. In some embodiments, solutions for providing a confidence-estimation-based inference are provided. Elements include receiving a query concerning a patient from a user; accessing an electronic health record (EHR) for the patient, the EHR including a first component regarding the patient; querying the user, using a conversational interface, for a second component regarding the patient; receiving the second component regarding the patient in response to the query; calculating a first probability density function using the first component, and a second probability density function using the second component; combining the first and second probability density functions using a Gaussian mixture model; calculating at least one conditional probability table using the Gaussian mixture model; and providing the confidence-estimation-based inference based on the at least one conditional probability table.

A first aspect provides a method of providing a confidence-estimation-based inference, the method comprising: receiving a query concerning a patient from a user; accessing an electronic health record (EHR) for the patient, the EHR including a first component regarding the patient; querying the user, using a conversational interface, for a second component regarding the patient; receiving the second component regarding the patient in response to the query; calculating a first probability density function using the first component, and a second probability density function using the second component; combining the first and second probability density functions using a Gaussian mixture model; calculating at least one conditional probability table using the Gaussian mixture model; and providing the confidence-estimation-based inference based on the at least one conditional probability table.

A second aspect provides a system comprising: at least one computing device configured to determine a providing a confidence-estimation-based inference by performing actions including: receiving a query concerning a patient from a user; accessing an electronic health record (EHR) for the patient, the EHR including a first component regarding the patient; querying the user, using a conversational interface, for a second component regarding the patient; receiving the second component regarding the patient in response to the query; calculating a first probability density function using the first component, and a second probability density function using the second component; combining the first and second probability density functions using a Gaussian mixture model; calculating at least one conditional probability table using the Gaussian mixture model; and providing the confidence-estimation-based inference based on the at least one conditional probability table.

A third aspect provides a computer program product comprising program code stored on a computer-readable storage medium, which when executed by at least one computing device, enables the at least one computing device to implement a method of providing a confidence-estimation-based inference by performing actions including: receiving a query concerning a patient from a user; accessing an electronic health record (EHR) for the patient, the EHR including a first component regarding the patient; querying the user, using a conversational interface, for a second component regarding the patient; receiving the second component regarding the patient in response to the query; storing the received second component in the EHR; calculating a first probability density function using the first component, and a second probability density function using the second component; combining the first and second probability density functions using a Gaussian mixture model; calculating at least one conditional probability table using the Gaussian mixture model; and providing the confidence-estimation-based inference based on the at least one conditional probability table.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION

The subject matter disclosed herein relates generally to medical records. More particularly, the subject matter disclosed relates to providing a confidence-based inference from evidence-based medical records and natural language input.

As differentiated from conventional medical diagnostic methods, the conversational Electronic Health Record (EHR) system, according to various embodiments enables the generation of deductive and inductive logic for a succinct answer given discovered knowledge. Embodiments of the invention provide seamless methods to utilize both text and multimedia information with an EHR. Various embodiments described herein allow for a single, natural language conversational system that aggregates and discovers knowledge from external question and answer systems. Furthermore, missing data may be retrieved by different methods from patients, medical professionals or related entities. According to aspects, statistical methods may be implemented to mix components together from probability density functions, in order to provide evidence-based decisions to inferences.

As discussed above, an Electronic Health Record (EHR) is used to store patient data for future recovery to assist in treatment plans. Different types of information derived from an EHR can be utilized to determine diagnosis, prognosis, or general health monitoring. EHRs provide standardized, accessible, and instantaneous patient data that are used by medical practitioners in health settings. In conjunction and with natural language-using, interactive computing systems, many NLP systems are providing answers to natural questions.

Given the accessibility of patient-related information in conjunction with an EHR, various embodiments provide systems that can interpolate from provided medical information, while extrapolating through conversations with a patient. The data gathered from the EHR and the patient may provide the system of various embodiments with information to synthesize a question for a question and answering system. Any responses back to the system may be delivered to the patient or owner of the EHR and stored for future evidence retrieval.

An Evidence-Based Medical Record (EBMR) knowledge chaining system may be described as a probabilistic inference reasoner that combines evidence. Various embodiments make use of an EMBR in conjunction with a system where information follows a natural language conversation paradigm that aggregates information from question and answering systems and human medical practitioners while generating questions from an EHR to apply against belief networks.

Figure 1:
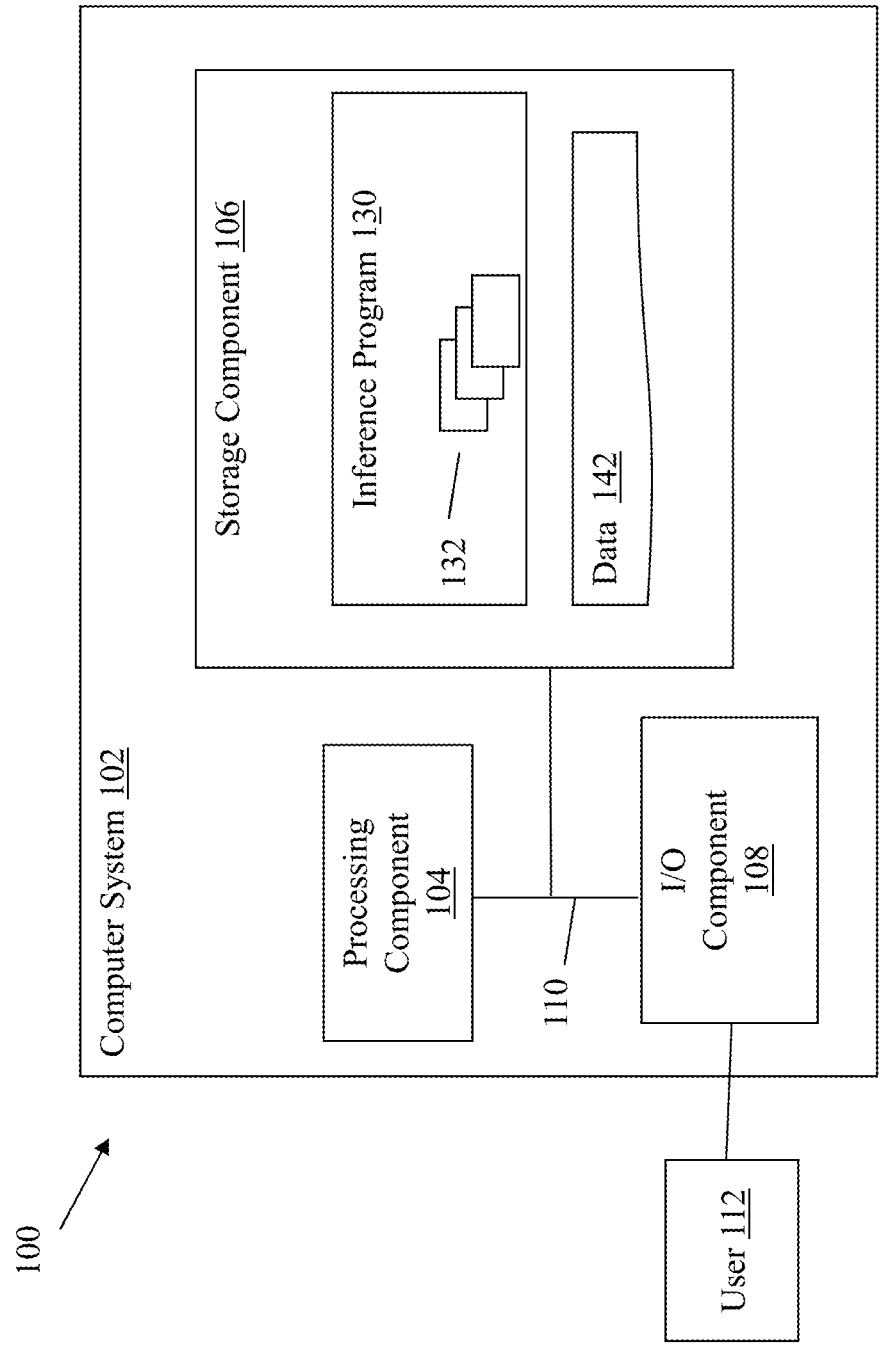
FIG. 1 shows an illustrative environment according to various embodiments.

Turning now to FIG. 1, an illustrative environment according to various embodiments is shown. FIG. 1 depicts an illustrative environment 100 for providing a confidence-based inference from evidence-based medical records and natural language input. To this extent, the environment 100 includes a computer system 102 that can perform a process described herein in order to provide a confidence-based inference. In particular, the computer system 102 is shown as including an inference program 130, which makes computer system 102 operable to handle all necessary calculations and functions by performing any/all of the processes described herein and implementing any/all of the embodiments described herein.

The computer system 102 is shown including a processing component 104 (e.g., one or more processors), a storage component 106 (e.g., a storage hierarchy), an input/output (I/O) component 108 (e.g., one or more I/O interfaces and/or devices), and a communications pathway 110. In general, the processing component 104 executes program code, such as the inference program 130, which may be at least partially fixed in the storage component 106. While executing program code, the processing component 104 can process data, which can result in reading and/or writing transformed data from/to the storage component 106 and/or the I/O component 108 for further processing. The pathway 110 provides a communications link between each of the components in the computer system 102. The I/O component 108 can comprise one or more human I/O devices, which enable a user 112 to interact with the computer system 102 and/or one or more communications devices to enable a system user 112 to communicate with the computer system 102 using any type of communications link. User 112 may be a human, including a health care professional, a patient, etc., or a non-human system. Inference program 130 can manage a set of interfaces (e.g., graphical user interface(s), application program interface, etc.) that enable human and/or system users 112 to interact with inference program 130. Further, the inference program 130 can manage (e.g., store, retrieve, create, manipulate, organize, present, etc.) data, such as ERH data 142, etc., using any solution. Inference program 130 includes a set of subcomponents 132 described below.

Figure 2:
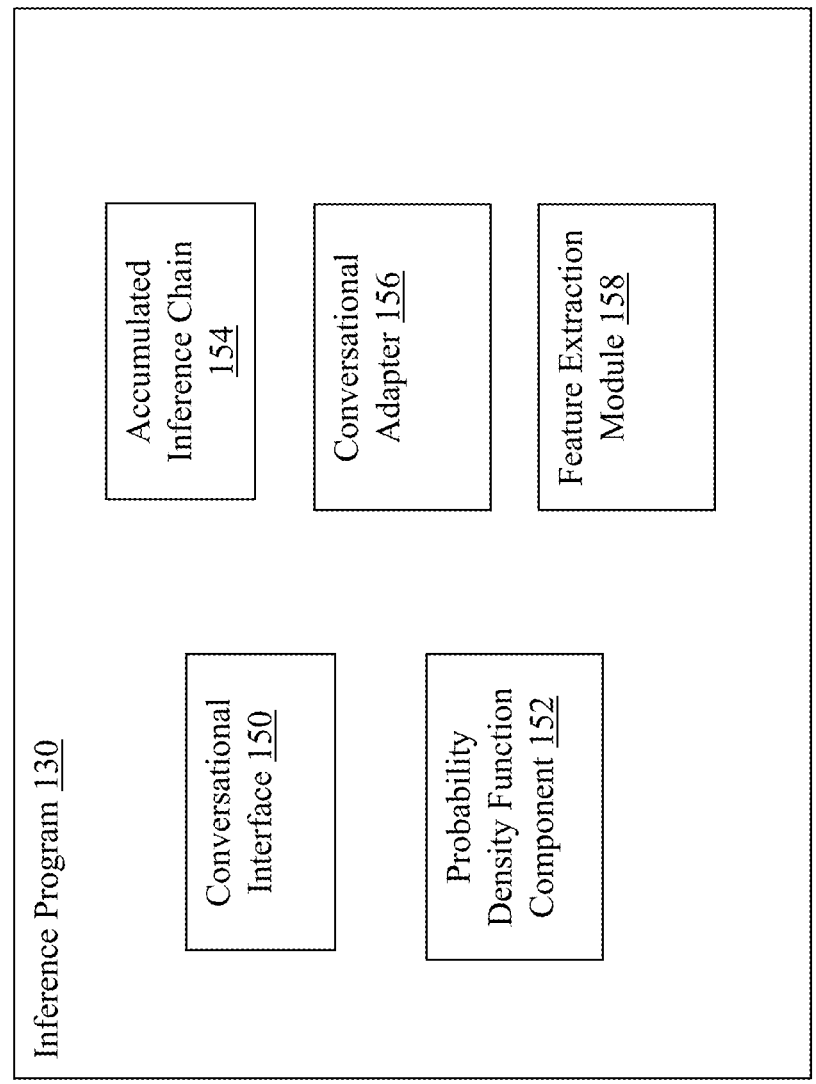
FIG. 2 shows subcomponents in an illustrative environment according to various embodiments.

FIG. 2 shows subcomponents 132 of inference program 130 in an illustrative environment according to various embodiments. The subcomponents 132 or modules are shown in relation to inference program 130, which provides the execution environment of computer system 102. Such subcomponents may include, but are not limited to a Conversational Interface 150, a Probability Density Function Component 152, an Accumulated Inference Chain 154, a Conversational Adapter 156, and at least one Feature Extraction Module 158. While these subcomponents or modules are illustrated as being within processing component 104, it should be understood that the locations of the subcomponents or modules is not limited to processing component 104. The subcomponents or modules may be located within different articles of manufacture and/or they maybe located remote from one another without deviating from the scope of the inventive concepts.

The Conversational Interface 150 is utilized to discover evidential information using external question and answering systems known questions and answer systems thus provide a knowledge elicitation from a user 12, e.g. a patient, a health care professional including a doctor, or other related entity.

The Probability Density Function Component 152 provides logic to build Probability Density Functions for mixing. The result of such mixing may be a score that provides a confidence estimation of a given agglomeration of hypothesis testing from feature extraction, given text and multimedia data within an EHR.

The Accumulated Inference Chain 154 is utilized for filling conditional probability tables with results of a plurality of probability density function components.

The Conversational Adapter 156 may enable the integration of external data sources for candidate answer generation and retention, where the candidate may be a patient. Each candidate answer contains features that are modeled with the Probability Density Function Component.

The at least one Feature Extraction Module 158 may be used to apply each textual sentence through an analytical pipeline for natural language processing and feature extraction. This textual feature extraction could, for example be provided by IBM Nuance's Clinical Language Understanding (CLU) natural language understanding products that are known in the art. Such natural language understanding products are able to automatically transcribe clinicians' dialogs, extracting the significant technical points from free speech. In conjunction, multimedia data may also go through a feature extraction stage. Here, for example, multimedia artifacts, such as x-rays and electrocardiographs readouts could be analyzed, having their features extracted using techniques known in the art, like that described in V. A. Mikhailov, and A. B. Vol'pert, "Automatic x-ray image recognition," Biomedical Engineering, May-June, 1981, Volume 15, Issue 3, pp. 67-71. In such techniques, a texture report is automatically generated containing a summary of all of the features found in the multimedia artifact, the x-ray. In any event, the computer system 102 can comprise one or more general purpose computing articles of manufacture (e.g., computing devices) capable of executing program code, such as the inference program 130, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the inference program 130 can be embodied as any combination of system software and/or application software.

Further, the inference program 130 can be implemented using a set of subcomponents 132. In this case, a subcomponent 132 can enable the computer system 102 to perform a set of tasks used by the inference program 130, and can be separately developed and/or implemented apart from other portions of the inference program 130. As used herein, with reference to the computer system hardware, the term "component" means any configuration of hardware, with or without software, which implements the functionality described in conjunction therewith using any solution, while the term "module" means program code that enables the computer system 102 to implement the functionality described in conjunction therewith using any solution. When fixed in a storage component 106 of a computer system 102 that includes a processing component 104, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 102.

When the computer system 102 comprises multiple computing devices, each computing device may have only a portion of inference program 130 fixed thereon (e.g., one or more modules 132). However, it is understood that the computer system 102 and inference program 130 are only representative of various possible equivalent computer systems that may perform a process described herein. To this extent, in other embodiments, the functionality provided by the computer system 102 and inference program 130 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 102 includes multiple computing devices, the computing devices can communicate over any type of communications link. Further, while performing a process described herein, the computer system 102 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 102 can obtain or provide EHR data 142; such data 142 may be used for any appropriate solution. For example, the computer system 102 can generate and/or be used to generate data 142, retrieve data 142, from one or more data stores, receive data 142 from another system, send 142 to another system, receive data 142 from a human or non-human user 112, etc.

Figure 3:
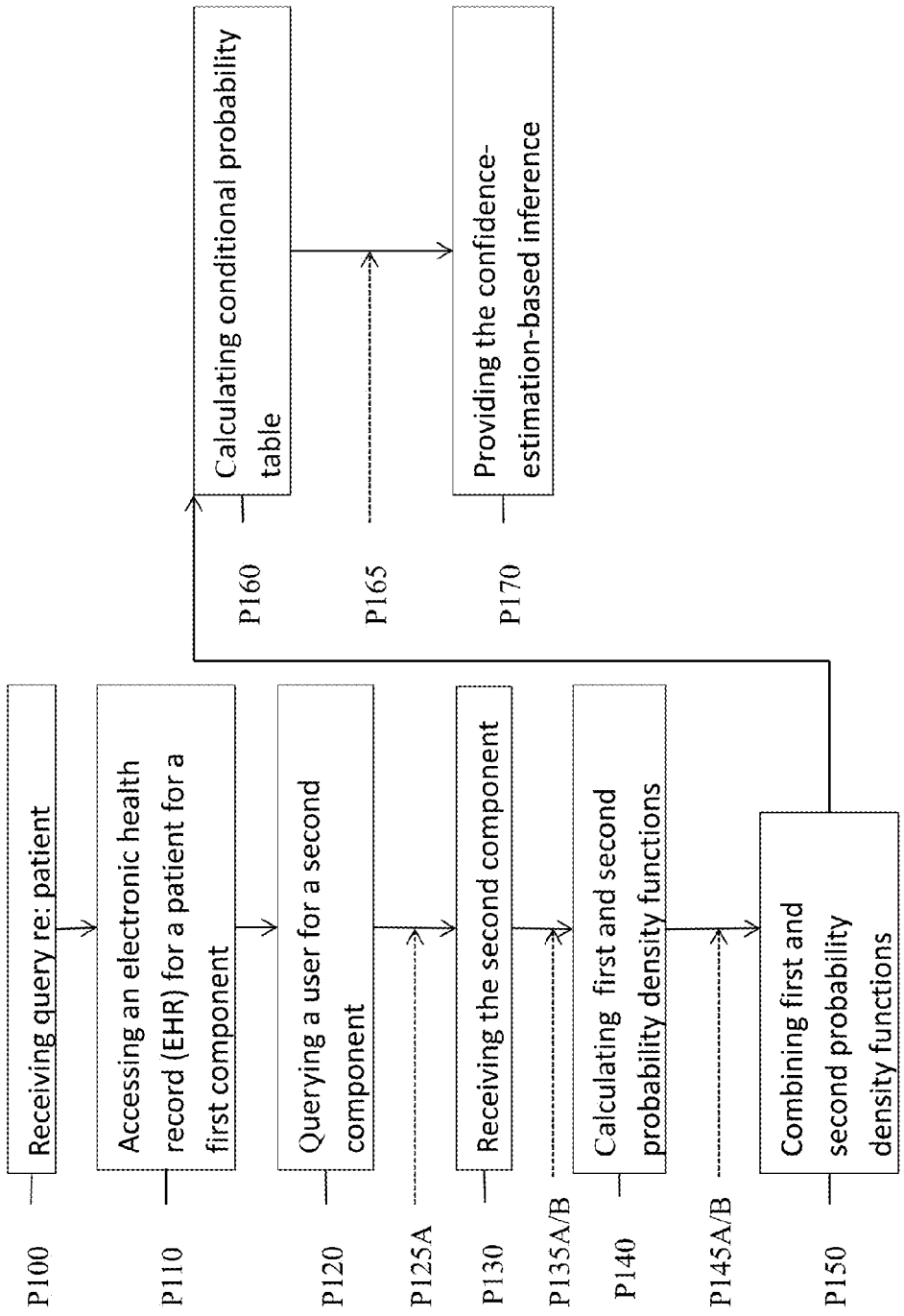
FIG. 3 shows a flow diagram illustrating a method according to various embodiments.

FIG. 3 shows a flow diagram illustrating a method according to various embodiments. The method illustrated provides a confidence-estimation-based inference according to aspects of the invention. Process P100 includes receiving a query concerning a patient from a user. The user may be a physician or the patient him/herself. According to aspects, the user first queries the system concerning a patient, and the system, after looking up the patient information, may later query the user for further information, as described in steps below. For example, "how old is the patient?" Process P110 includes accessing an electronic health record (EHR) for a patient, the EHR including a first component regarding the patient The first component regarding the patient, (in this example, "age"), is also referred to herein as "evidence" and the terms "evidence" and "component regarding the patient" may be used interchangeably. An illustrative EHR is described above and may include components such as health-related data, family history or other information related to a patient. The types of data, i.e. components, which may be contained in the EHR is not limited.

Also illustrated in FIG. 3, process P120 includes querying a user 112 (user 112 shown in FIG. 1), using a conversational interface, for a second component regarding the patient, the second component being in a natural language information form. For example, the system could query the physician, "is the patient coughing?" The user 112 may be one of a health care professional, the patient, or a non-human system; however, the user 112, according to embodiments is not limited to such entities and may include any person or system capable of interacting with the system to respond to the query via the conversational interface.

Process P130 includes receiving the second component regarding the patient in response to the query. The second component may be received using a conversational interface 150 and/or a conversational adapter 156, both of which are illustrated in FIG. 2. The conversational interface 150 and the conversational adapter 156 may utilize NLP capabilities.

Process P140 includes calculating a first probability density function using the first component, and a second probability density function using the second component. Each probability density function describes the relative likelihood that a variable, e.g. age, will take on a given value.

Process P150 includes combining the first and second probability density functions using a Gaussian mixture model. Process P160 includes calculating at least one conditional probability table using the Gaussian mixture model. Probability density function component 152, illustrated in FIG. 2, may be used to compute these functions. An illustrative Bayesian network based on at least one conditional probability table is shown below in FIG. 7. A conditional probability tables are tables that include data representing the likelihood that a second event will occur, given the prior occurrence of a first event or state. Conditional probability tables may include conditional probability outcomes.

Process P170 includes providing the confidence-estimation-based inference based on the at least one conditional probability table. The inference may be a medical diagnosis or a medical prognosis regarding the patient. The inference may also be any type of conclusion a healthcare professional or the patient may desire to know, based on the patient's current or future condition, such as whether a given medication will eventually lead to future complications or become ineffective.

Figure 4:
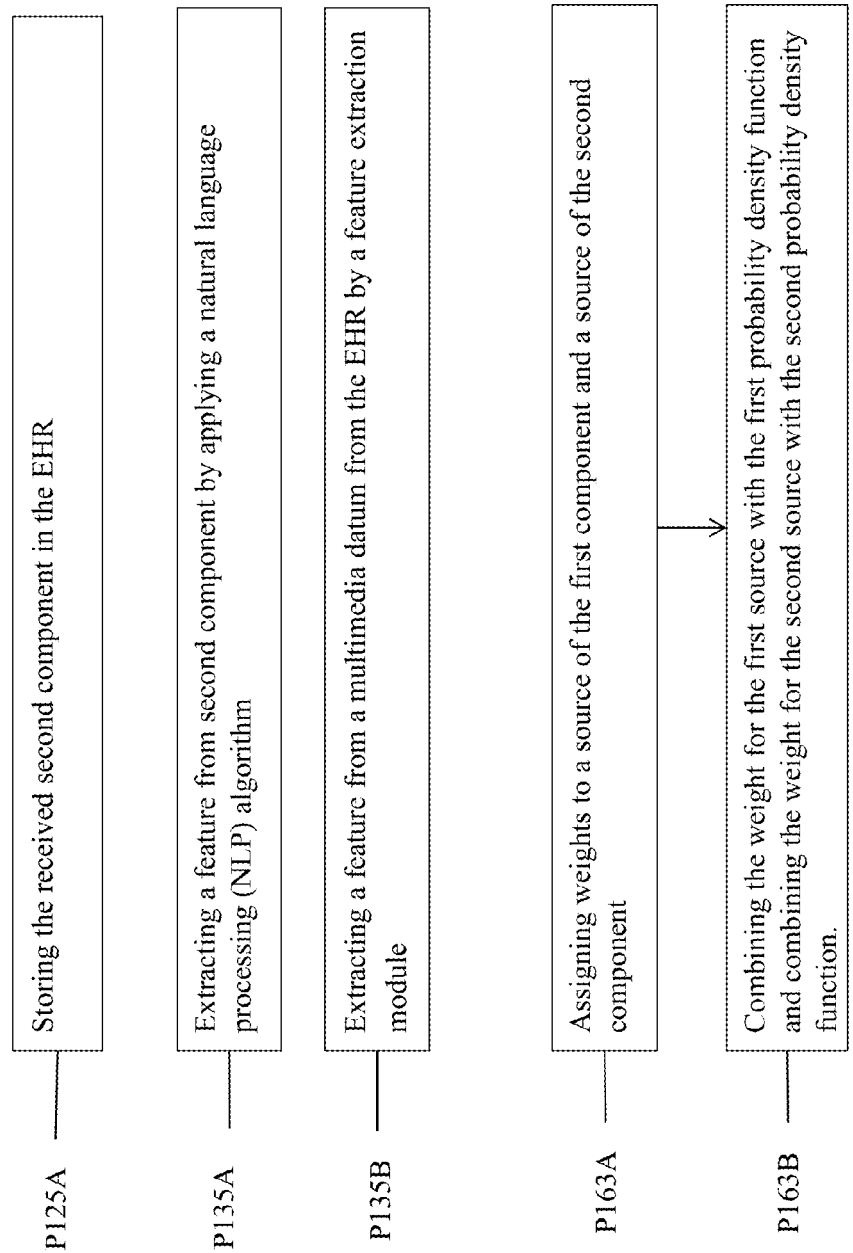
FIG. 4 shows flow diagram components illustrating optional processes that may be performed in conjunction with methods according to various embodiments.

FIG. 4 shows flow diagram components illustrating optional processes that may be performed in conjunction with methods according to various embodiments. FIG. 4 illustrates optional process P125A, which includes storing the received second component in the EHR. The received second component may be stored in the EHR for later retrieval, for simple completion of a health record or for other reasons. FIG. 4 further illustrates optional processes 135A and 135B. Optional process 135A includes extracting at least one feature from the natural language information by applying a natural language processing (NLP) algorithm to the natural language information. This textural extraction from the natural language information could be provided by transcription products known in the art. Optional process 135B includes extracting at least one feature from a multimedia datum from the EHR by a feature extraction module. Feature extraction module 158, illustrated in FIG. 2 may be used for this process. One exemplary method for providing the multi feature extraction from multimedia datum includes that described by Xiao Dong, Miguel A. Gonzalez Ballester, Guoyan Zheng, "Automatic Extraction of Femur Contours from Calibrated X-Ray Images using Statistical Information," JOURNAL OF MULTIMEDIA, VOL. 2, NO. 5, SEPTEMBER 2007, which automatically provides a textual description of bone contours displayed in a given x-ray image.

Figure 5:
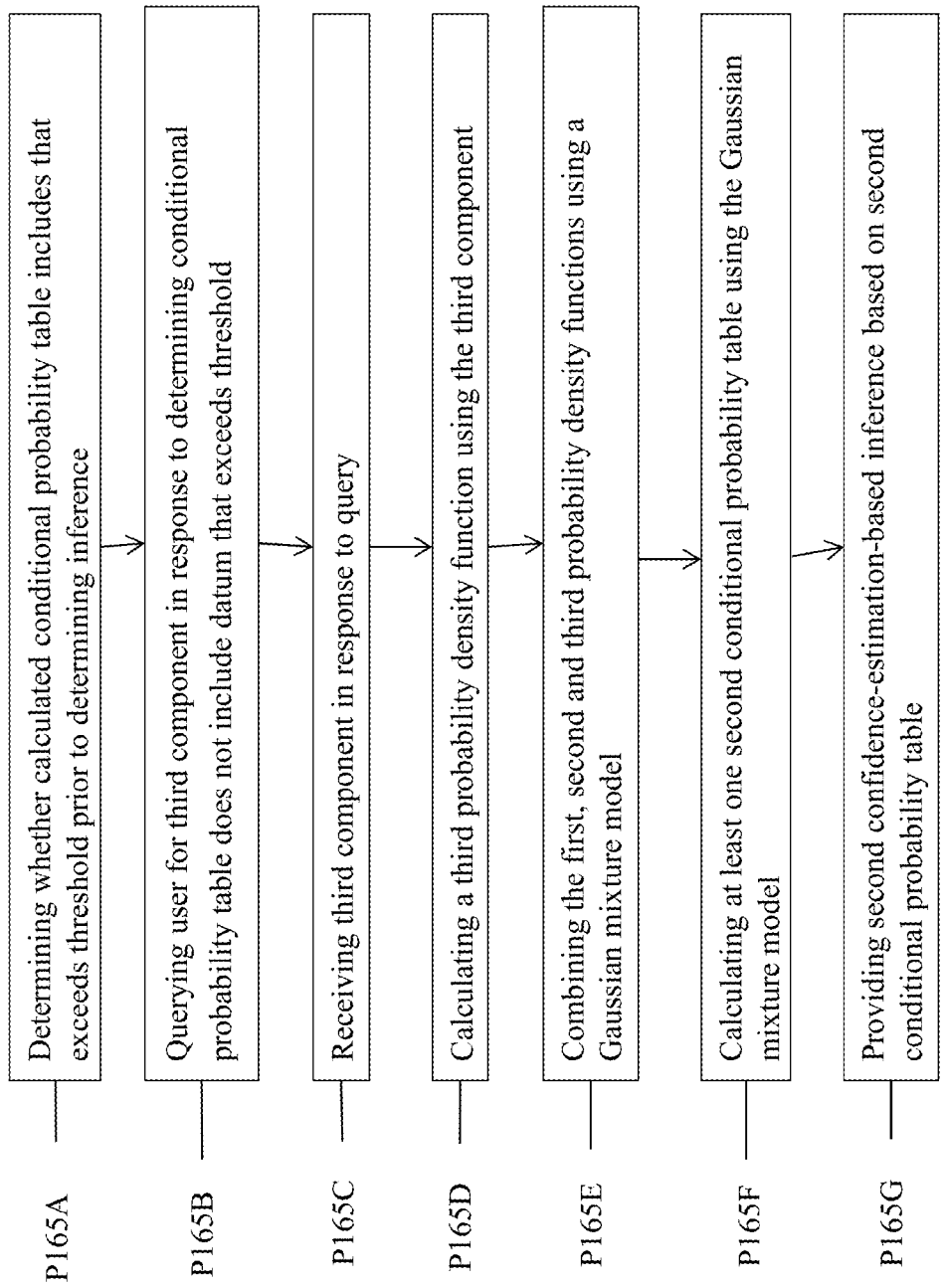
FIG. 5 shows flow diagram components illustrating optional processes that may be performed in conjunction with methods according to various embodiments.

FIG. 5 shows flow diagram components illustrating optional processes P165A-G that may be performed in conjunction with methods according to various embodiments. Optional process P165A includes determining whether the calculated at least one conditional probability table includes a probability datum that exceeds a threshold, prior to determining the inference. Optional process P165B includes querying a user for a third component regarding the patient in response to determining that the at least one conditional probability table does not include the probability datum that exceeds the threshold.

Optional process 165C includes receiving the third component in response to the querying for the third component. Optional process 165D includes calculating a third probability density function using the third component. Optional process 165E includes combining the first, second and third probability density functions using a Gaussian mixture model. Optional process 165F includes calculating at least one second conditional probability table using the Gaussian mixture model. Optional process 165G includes providing a second confidence-estimation-based inference based on the at least one second conditional probability table. These processes may be carried out, as described above, by conversational interface 150, conversational adapter 156, and probability density function component 152, as appropriate.

Figure 6:
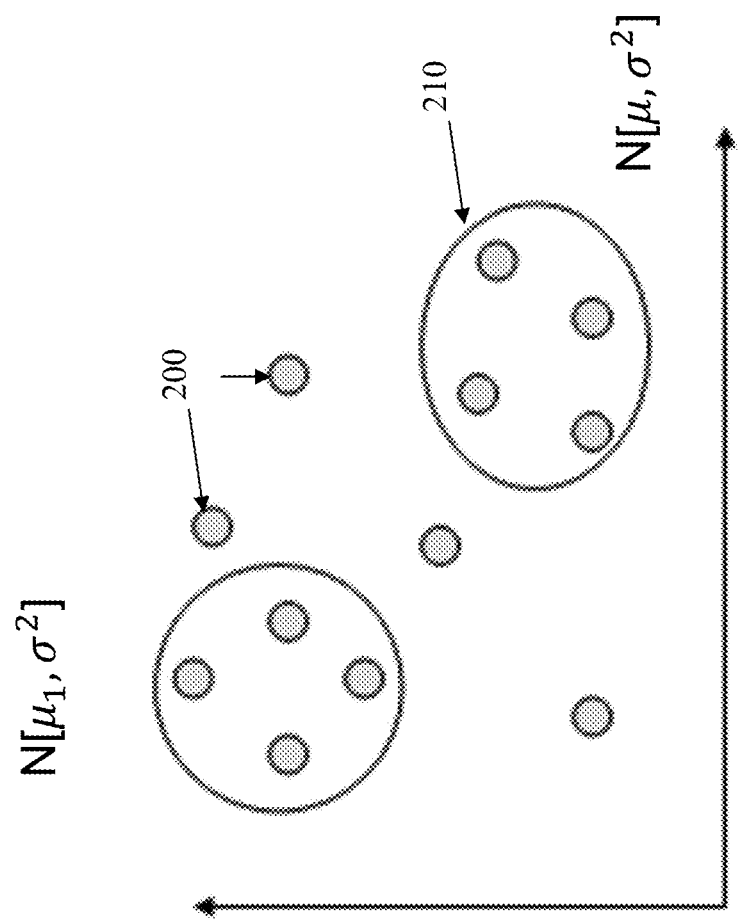
FIG. 6 illustrates illustrative Gaussian distributions according to various embodiments.

FIG. 6 depicts an illustrative Gaussian distribution according to various embodiments. These Gaussian distributions represent responses 200 from question and answer sessions according to embodiments. For example, the natural question from a patient who has an EHR could be "Do I have the flu?" The original questions may be expanded to include electronic health record information to: "Do I have the flu when my temperature is 100 degrees?" Alternatively, a perpetual query from the EHR helps to generate more evidence for "What are common fevers for the flu?" The responses generated over time could be fever at 102, fever at 94, fever at 105, etc. The responses from each question and answer system are clustered together into component clusters 210, as shown in FIG. 6.

The fever component cluster 210 would be fit into a Gaussian Mixing Model such that when the fever reading is taken from an EHR, a probability is output. Mixing coefficients which set the relative contribution of a probability score from multiple Natural Language Processing (NLP) systems may be used in conjunction with this process. For example, if four component clusters 210 were created from four separate systems, the mixing coefficients combine the results. Other illustrative symptoms, based on component clusters 210, such as heart rate product Gaussian Mixture Models (GMM's) may be utilized, but are not shown for the sake of simplicity.

According to embodiments, a belief, or inference, is created by combining all probabilities from symptoms over the accumulation of evidence. In an example with six clusters, a response from the system given features from the EHR could be "You have a fever, normal heart rate, live in a region susceptible to the flu, you have aches, stuffed sinuses, and a head ache. Therefore, with x % confidence, you have the flu."

In the above example, a feature vector would be described as follows:

x=temperature, heart rate, locale, aches, stuffed sinuses, head ache.

According to aspects, for each feature within feature vector from an EHR, a Gaussian Model is built from candidate answers retrieved by external question and answering systems. Each feature dimension is modeled by Gaussian Models, as shown below.

$$N(x_i, \mu_j, \sigma_j^2 I) = \frac{1}{e\sqrt{2\pi}} e^{\frac{(x_i - u_j)^2}{2\sigma_j^2}}$$

For the example component, hypothesis testing begins with the closest cluster that matches a question. The null hypothesis claims that the closest cluster (i.e. $N(x_i, \mu_j, \sigma_j^2 I)$) does not sufficiently fit the Gaussian model. In this case, $H_0 = N(x_i, \mu_j, \sigma_j^2 I)$, $\sigma^2 < N(x_i, \mu_j, \sigma_j^2 I) < 68\%$. If the null hypotheses $H_o$ is rejected, then $H_o = N(x_i, \mu_j, \sigma_j^2 I)$, $\sigma^2 \geq N(x_i, \mu_j, \sigma_j^2 I) \geq 68\%$. After each component or feature $x_i$, has passed a null hypothesis test, the density scores are combined or mixed $$p(\bar{x}|\lambda) = \sum_{i=1}^{M} \omega_i p_i(x)$$

where $M=|\bar{x}|$ and $\lambda=\{\omega_i, \mu_j, \Sigma_j\}$ of a Gaussian distribution, for example, as follows:

It should be noted that the mixing coefficient, $\omega_j$, sets the relative weights for each components where $$\sum_{i=1}^{M} \omega_i = 1.$$

The final numerical score of $p(\bar{x}|\lambda) \in [0,1]$ and provides a confidence for a particular set of symptoms According to aspects, an inference may be made using a combination of symptoms, related diseases, and patient facts, e.g., facts or components from the patient's EHR. The inference arrived at uses a Bayesian network as illustrated in FIG. 7.

Figure 7:
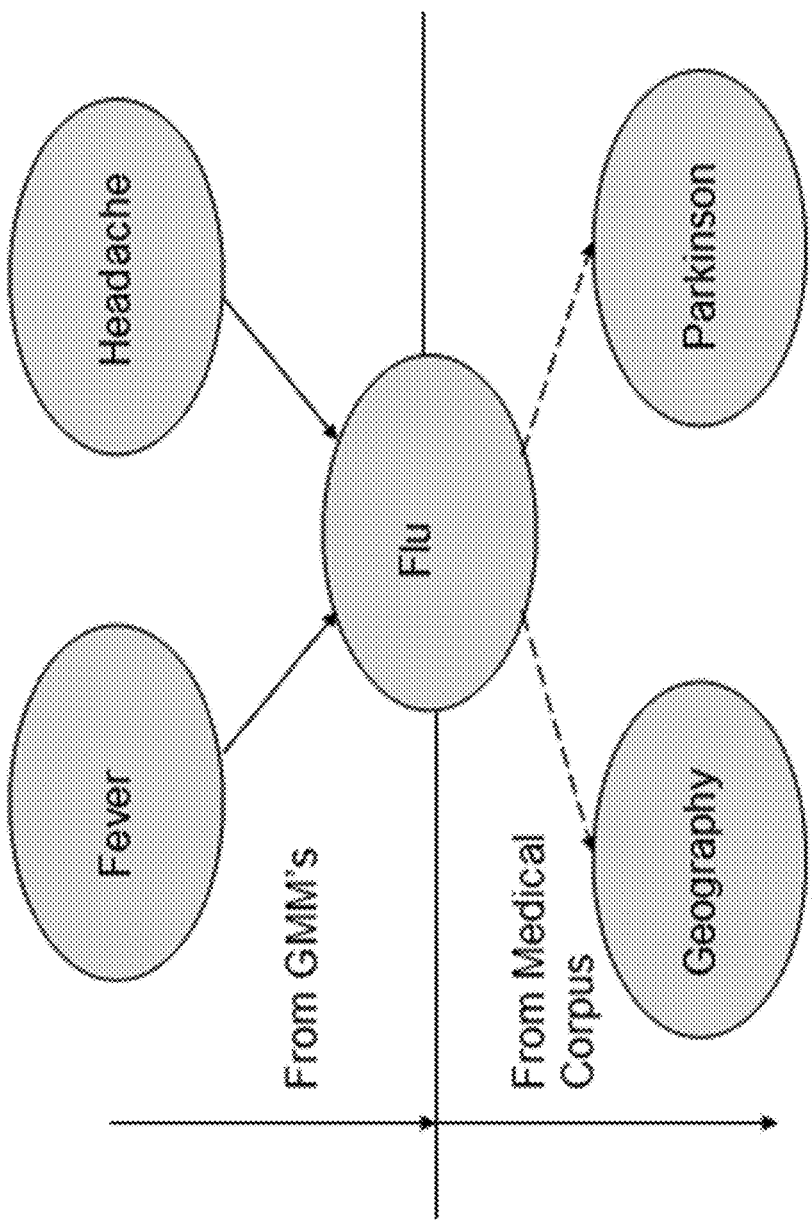
FIG. 7 illustrates an illustrative Bayesian network according to various embodiments.

FIG. 7 illustrates an illustrative Bayesian network according to various embodiments and is a graphical representation of an inference tool according to various embodiments. Bayesian network 300 illustrates a set of random variables, including fever and headache and their conditional dependencies. The states "Fever" and "Headache" are prior or existing conditions that can contribute to the contraction or the existence of the "Flu". The solid arrows represent the conditioning of "Flu" on a patient's ailment. The states "Geography" and "Parkinson" are conditioned on "Flu". The probability that an individual lives in a certain geography depends on if that person has the flu as represented by the dotted line. The states "Fever" and "Parkinson" are only associated together through "Flu". States are formed through evidence stratified to discern higher and lower probability outcomes about the flu. If, during the model building from external question and answer sources, a feature or component has been discovered that is not present within the EHR, the system may elicit information from the patient or health care provider/professional. The conversational transaction may discover more evidence and include the feature within the feature vector. If needed or desired information is still missing, the component is not used and the remaining components are re-weighted.

Use Case 1—Patient Using System:

In this example, a patient interacts with the system by inputting relevant information which may include his or her vital signs. The patient asks health-related questions using a natural language conversational interface. If the system determines that more information is needed in order to give an answer with more confidence, the system will ask the patient for such information.

Use Case 2—Physician Using System:

In this example, a physician may begin by interacting with the system by inputting patient information and asking the patient questions related to the patient's health. As above, if the system determines that it needs some information to give an answer with more confidence, it will ask the physician via a conversational interface. The physician may choose to ignore any questions deemed irrelevant.

Use Case 3—Physician and Patient Using the System:

According to this example, a patient and a health care professional may interact with the system together by inputting patient information and vital signs. Both users, the patient and the health care professional, may ask the system questions related to the patients health.

While shown and described herein as a method and system for providing a confidence-based inference from evidence-based medical records and natural language input, it is understood that aspects of the invention further provide various alternative embodiments. For example, in one embodiment, the invention provides a computer program fixed in at least one computer-readable medium, which when executed, enables a computer system to perform a method of determining a characteristic of an optical mask. To this extent, the computer-readable medium includes program code, such as inference program 130 (FIG. 1), which implements some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of determining a characteristic of an optical mask using optical metrology data and simulation data. In this case, a computer system, such as computer system 102 (FIG. 1), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; and/or the like.

It is understood that aspects of the invention can be implemented as part of a business method that performs a process described herein on a subscription, advertising, and/or fee basis. That is, a service provider could offer to characterize an optical mask as described herein. In this case, the service provider can manage (e.g., create, maintain, support, etc.) a computer system, such as computer system 102 (FIG. 1), that performs a process described herein for one or more customers. In return, the service provider can receive payment from the customer(s) under a subscription and/or fee agreement, receive payment from the sale of advertising to one or more third parties, and/or the like.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of providing a confidence-estimation-based inference, the method comprising:
   receiving a query concerning a patient from a user;
   accessing an electronic health record (EHR) for the patient, the EHR including a first component regarding the patient;
   querying the user, using a conversational interface, for a second component regarding the patient;
   receiving the second component regarding the patient in response to the query;
   calculating a first probability density function using the first component, and a second probability density function using the second component;
   combining the first and second probability density functions using a Gaussian mixture model;
   calculating at least one conditional probability table using the Gaussian mixture model; and
   providing the confidence-estimation-based inference based on the at least one conditional probability table.

2. The method of claim 1, wherein the inference is one of a medical diagnosis or a medical prognosis.

3. The method of claim 1, wherein the at least one computing device is further configured to perform actions including:
   storing the received second component in the EHR.

4. The method of claim 1, wherein the at least one computing device is further configured to perform actions including:
   prior to determining the inference, determining whether the calculated at least one conditional probability table includes a probability datum that exceeds a threshold;
   querying a user for a third component regarding the patient in response to determining that the at least one conditional probability table does not include the probability datum that exceeds the threshold;
   receiving the third component in response to the querying for the third component;
   calculating a third probability density function using the third component;
   combining the first, second and third probability density functions using a Gaussian mixture model;
   calculating at least one second conditional probability table using the Gaussian mixture model; and
   providing a second confidence-estimation-based inference based on the at least one second conditional probability table.

5. The method of claim 1, wherein the second component is in a natural language information form, the method further comprising extracting at least one feature from the natural language information by applying a natural language processing (NLP) algorithm to the natural language information.

6. The method of claim 1, further comprising:
   extracting at least one feature from a multimedia datum from the EHR by a feature extraction module.

7. The method of claim 1, wherein the user is one of a health care professional, the patient, or a non-human system.

8. The method of claim 1, wherein the at least one computing device is further configured to perform actions including:
   assigning a first weight to a source of the first component;
   assigning a second weight to a source of the second component, wherein the
   weights sum to one hundred percent; and
   mathematically combining the weight for the first source with the first probability density function and mathematically combining the weight for the second source with the second probability density function.

9. A system comprising:
   at least one computing device configured to determine a confidence-estimation-based inference by performing actions including:
   receiving a query concerning a patient from a user;
   accessing an electronic health record (EHR) for the patient, the EHR including a first component regarding the patient;
   querying the user, using a conversational interface, for a second component regarding the patient;
   receiving the second component regarding the patient in response to the query;
   calculating a first probability density function using the first component, and a second probability density function using the second component;
   combining the first and second probability density functions using a Gaussian mixture model;
   calculating at least one conditional probability table using the Gaussian mixture model; and
   providing the confidence-estimation-based inference based on the at least one conditional probability table.

10. The system of claim 9, wherein the inference is one of a medical diagnosis or a medical prognosis.

11. The system of claim 9, wherein the at least one computing device is further configured to perform actions including:
    storing the received second component in the EHR.

12. The system of claim 9, wherein the at least one computing device is further configured to perform actions including:
    prior to determining the inference, determining whether the calculated at least one conditional probability table includes a probability datum that exceeds a threshold;
    querying a user for a third component regarding the patient in response to determining that the at least one conditional probability table does not include the probability datum that exceeds the threshold;
    receiving the third component in response to the querying for the third component;
    calculating a third probability density function using the third component;
    combining the first, second and third probability density functions using a Gaussian mixture model;
    calculating at least one second conditional probability table using the Gaussian mixture model; and providing a second confidence-estimation-based inference based on the at least one second conditional probability table.

13. The system of claim 9, wherein the second component is in a natural language information form, wherein the at least one computing device is further configured to perform actions including:
   extracting at least one feature from the natural language information by applying a natural language processing (NLP) algorithm to the natural language information; and
   extracting at least one feature from a multimedia datum from the EHR by a feature extraction module.

14. The system of claim 9, wherein the user is one of a health care professional, the patient, or a non-human system.

15. The system of claim 9, wherein the at least one computing device is further configured to perform actions including:
   assigning a first weight by a user, to a source of the first component;
   assigning a second weight, by a user, to a source of the second component, wherein the weights sum to one hundred percent; and
   mathematically combining the weight for the first source with the first probability density function and mathematically combining the weight for the second source with the second probability density function.

16. A computer program product comprising program code stored on a non-transitory computer-readable medium, which when executed by at least one computing device, enables the at least one computing device to implement a method of providing a confidence-estimation-based inference by performing actions including:
   receiving a query concerning a patient from a user;
   accessing an electronic health record (EHR) for the patient, the EHR including a first component regarding the patient;
   querying the user, using a conversational interface, for a second component regarding the patient;
   receiving the second component regarding the patient in response to the query;
   storing the received second component in the EHR;
   calculating a first probability density function using the first component, and a second probability density function using the second component;
   combining the first and second probability density functions using a Gaussian mixture model;
   calculating at least one conditional probability table using the Gaussian mixture model; and
   providing the confidence-estimation-based inference based on the at least one conditional probability table.

17. The computer program product of claim 16, wherein the inference is one of a medical diagnosis or a medical prognosis.

18. The computer program product of claim 16, wherein the program code causes the at least one computing device to further perform actions including:
   prior to determining the inference, determining whether the calculated at least one conditional probability table includes a probability datum that exceeds a threshold;
   querying a user for a third component regarding the patient in response to determining that the at least one conditional probability table does not include the probability datum that exceeds the threshold;
   receiving the third component in response to the querying for the third component;
   calculating a third probability density function using the third component;
   combining the first, second and third probability density functions using a Gaussian mixture model;
   calculating at least one second conditional probability table using the Gaussian mixture model; and
   providing a second confidence-estimation-based inference based on the at least one second conditional probability table.

19. The computer program product of claim 16, wherein the second component is in a natural language information form, wherein the program code causes the at least one computing device to further perform actions including:
   extracting at least one feature from the natural language information by applying a natural language processing (NLP) algorithm to the natural language information; and
   extracting at least one feature from a multimedia datum from the EHR by a feature extraction module.

20. The computer program product of claim 16, wherein the program code causes the at least one computing device to further perform actions including:
   assigning a first weight by a user, to a source of the first component;
   assigning a second weight, by a user, to a source of the second component, wherein the weights sum to one hundred percent; and
   mathematically combining the weight for the first source with the first probability density function and mathematically combining the weight for the second source with the second probability density function.

\* \* \* \* \*